United States Patent [19]

Lambert

[11] Patent Number: 4,506,677
[45] Date of Patent: Mar. 26, 1985

[54] INDICATING DEVICE FOR DEFIBRILLATORS

[75] Inventor: Willibrordus J. S. Lambert, Eersel, Netherlands

[73] Assignee: Honeywell Inc., Minneapolis, Minn.

[21] Appl. No.: 452,181

[22] Filed: Dec. 21, 1982

[51] Int. Cl.³ .............................................. A61B 5/04
[52] U.S. Cl. ................................ 128/697; 128/419 D
[58] Field of Search ............ 128/419 D, 419 PT, 697, 128/702–704, 706, 710, 711

[56] References Cited

U.S. PATENT DOCUMENTS

| | | | |
|---|---|---|---|
| 3,221,334 | 11/1965 | Jones, Jr. ............................ | 128/711 |
| 3,897,774 | 8/1975 | Burdick et al. ................ | 128/419 PT |
| 4,109,243 | 8/1978 | Day et al. ............................ | 128/710 |
| 4,236,523 | 12/1980 | Gruenenwald ................ | 128/419 PT |
| 4,316,472 | 2/1982 | Mirowski et al. ................ | 128/419 P |
| 4,328,808 | 5/1982 | Charbonnier et al. ......... | 128/419 D |

*Primary Examiner*—William E. Kamm
*Attorney, Agent, or Firm*—Mitchell J. Halista; Trevor B. Joike

[57] ABSTRACT

An indicating device is used to record the waveshape of the patient current of a defibrillator as a composite with an ECG recording such that the current waveshape is shown clearly and can be evaluated. A coupling device is provided for deriving an electrical signal corresponding to the defibrillator current. The electrical signal is written at a high frequency into a memory for storage. A time extension of the stored signal is achieved subsequently by reading the stored signal from the memory with a low reading frequency. The ratio of the high and low frequencies is 100 to 1. The time extended signal is selectively applied for recording. During the duration of the recording of the defibrillator current waveshape, a switch control circuit interrupts the recording of the electrocardiogram (ECG) and substitutes the extended signal. A timing and delay circuit is used to synchronize the memory operation and the ECG interruption with the defibrillator operation.

9 Claims, 2 Drawing Figures

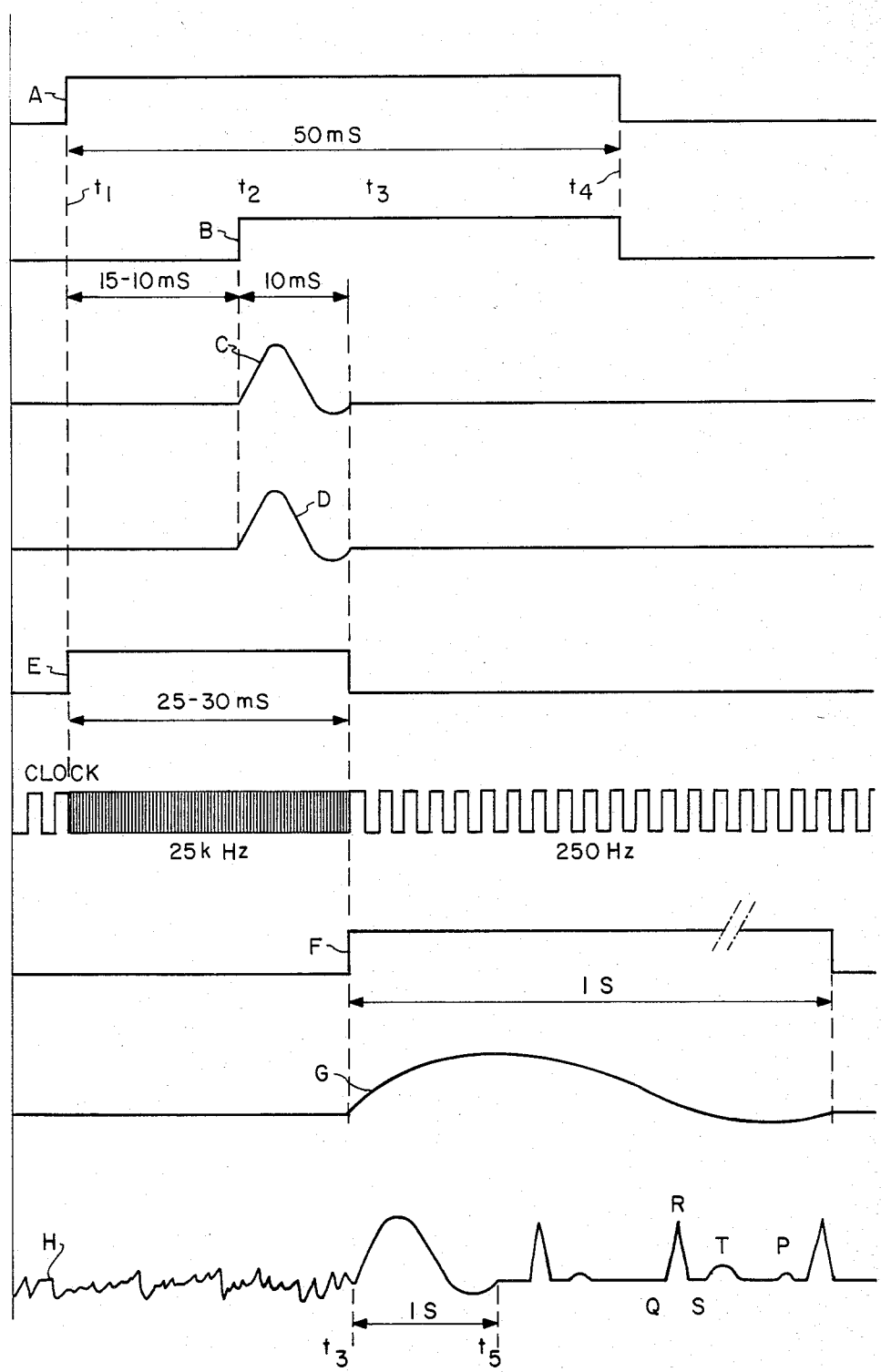
F I G. 2

INDICATING DEVICE FOR DEFIBRILLATORS

BACKGROUND OF THE INVENTION

Field of the Invention

The present invention relates to defibrillators. More specifically, the present invention is directed to defibrillator current pulse indicators.

SUMMARY OF THE INVENTION

An object of the present invention is to provide an improved defibrillator current pulse indicator.

In accomplishing this and other objects, there has been provided, in accordance with the present invention, an indicating device for a defibrillator including a coupling means for producing an electrical signal corresponding to a defibrillator current applied to a patient, memory means for receiving and storing the signal from the coupling means, memory operation control circuit means for writing the signal into the memory means and for reading the signal from the memory means to produce a time extended version of the signal and a control circuit means for interrupting a display of an ECG of the patient on an indicating means and substituting the time extended version of the signal for the interrupted ECG.

BRIEF DESCRIPTION OF THE DRAWINGS

A better understanding of the present invention may be had when the following detailed description is read in connection with the accompanying drawings, in which, FIG. 2 is a waveshape diagram showing the signal waveshapes occurring during the operation of the indicating device shown in FIG. 1.

DESCRIPTION OF THE PREFERRED EMBODIMENT

Detailed Description

Figure 1:
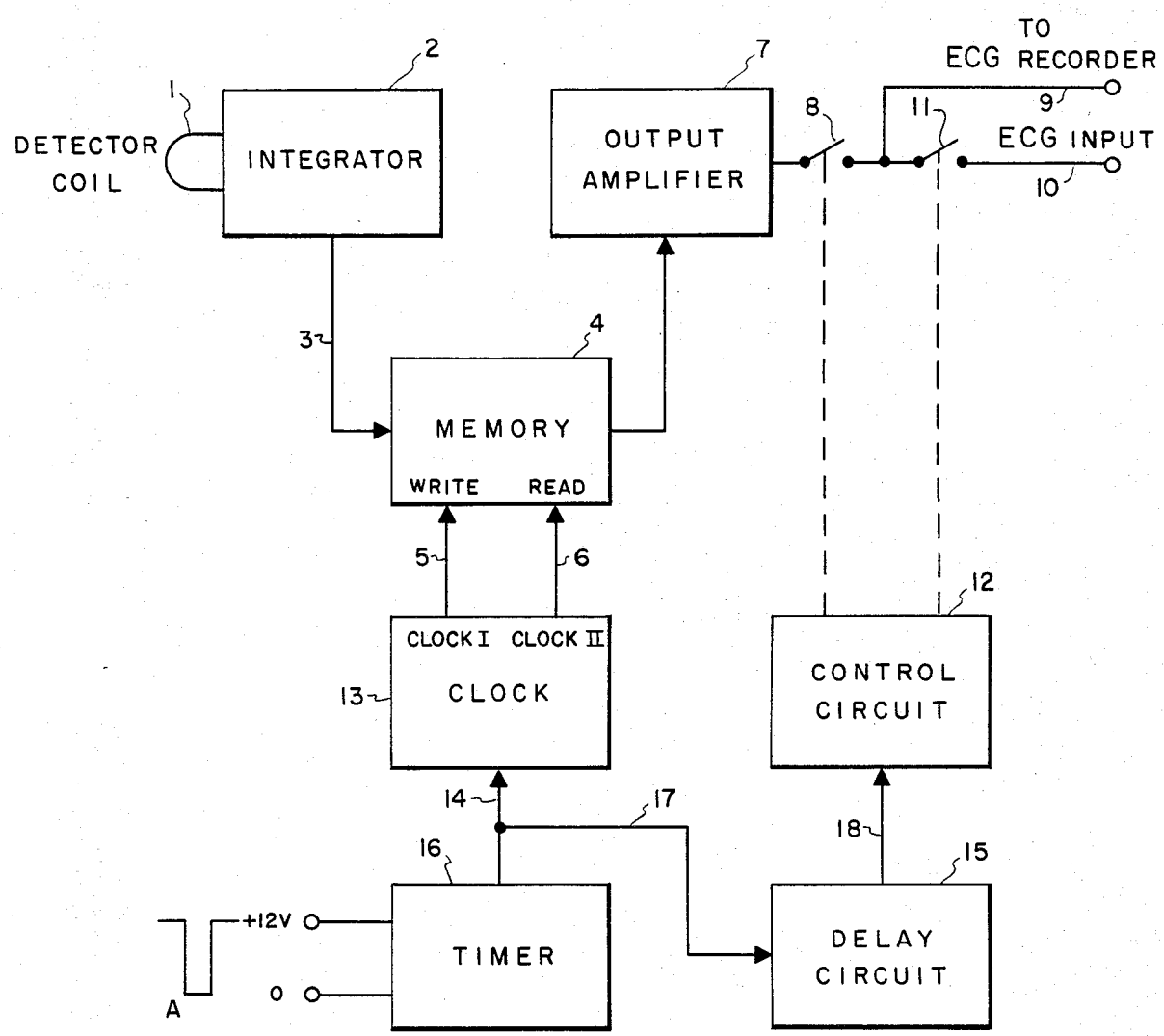
FIG. 1 is a block diagram of an indicating device for a defibrillator current pulse embodying an example of the present invention.

When defibrillating a patient, an ECG from the patient is usually recorded before and after the treatment. Furthermore, the manually adjustable defibrillator energy is measured. For better monitoring and judging of a defibrillation, a recording of the time dependent current curve of the defibrillator pulse would be useful. From this recording, one could determine the peak value of the defibrillator current, the electrical resistance of the patient as well as the energy supplied during the defibrillation. Since a typical defibrillator current pulse of six milliseconds is very short compared to the individual peaks of the ECG, it would appear in a nonextended record of the current pulse only as a dash within the ECG recording and, therefore, would not show its time dependent curve. The present invention provides a time extension of a representation of the waveshape of the defibrillator pulse and inserts a record of its extended waveshape into the running record of the ECG such that the ECG is recorded without disturbance before as well as after the defibrillation. For example, when recording the ECG on a strip recorder with a paper speed of 2.5 cm/s, it is advisable to extend in time the aforesaid defibrillator pulse of six milliseconds by a factor of 100 and to insert it into the ECG record for about one second.

The defibrillator current pulse for the patient usually is provided by a circuit (not shown) which includes a transmission capacitor that has been charged to a predetermined voltage and then is selectively connected by a pair of electrodes to a patient circuit (not shown). In the patient circuit, in most cases, a reactance coil is provided. To derive an electrical signal corresponding to the shape of the defibrillator current pulse, a current transducer can be inserted into the patient circuit. Alternatively, the coil reactance which determines the current through the patient can be provided with an additional coupling coil 1 as a current detector with the output from the coil 1 being connected to the input of an integrator 2. By an integration of the signal derived from the coil 1, an electrical signal corresponding to the time dependent curve of the current through the patient is available on an output line 3 of integrator 2. This integrator signal is applied to an analog memory 4 having two clock inputs 5 and 6 to which different clocking frequencies are selectively applied. The analog memory is connected via an output amplifier 7 and a switch 8 to the recording input 9 of an ECG recorder or indicator.

The ECG signal from the patient is received at input terminal 10 which, via a second switch 11, is also connected to the recording input of the ECG recorder. The two switches 8 and 11 are alternately switched by means of a control circuit 12. They are shown in FIG. 1 as mechanical switching contacts, but, in practice, they would be preferably electronic switches, for instance field effect transistors (FET). A clock 13 selectively delivers on the two clock lines 5 and 6 clock pulses Clock I and Clock II of different frequencies, e.g., a high frequency clock of 25 KHz is used for writing the integrator output signal into the analog memory 4 while a reading of the memory content and its transmission to amplifier 7 is done with a low frequency clock of 250 Hz. An input of a delay circuit 15 is connected to a control input line 14 of the clock 13 by line 17 while an output of the delay circuit 15 is connected to the control input line 18 of the control circuit 12. A voltage dependent timer 16 is connected to supply a control signal on the control input line 14 in response to a defibrillation command signal.

MODE OF OPERATION

The operation of this circuit will now be described with reference to FIGS. 1 and 2. In this connection, it is assumed that there is some period of time between the command signal initiating the defibrillation and the actual start of the current flow through the patient and that this period of time depends on the supply voltage of the defibrillator relay. This time delay is compensated for by the voltage dependent timer 16. It is assumed that at time $t_1$ the command for defibrillation is initiated by a signal pulse A as shown in FIG. 2. This pulse in the illustrated embodiment extends over fifty milliseconds. Switching over of the transmission capacitor supplying the patient current is achieved by means of a relay (not shown) after an initiating delay of fifteen to twenty milliseconds at time $t_2$. The defibrillator relay in accordance with signal B remains energized until the end of control pulse A at time $t_4$. Following the switching over of the transmission capacitor at time $t_2$, the current C through the patient starts to flow. This current flow lasts for about six to ten milliseconds and is finished at time $t_3$.

The coupling coil 1 produces a signal corresponding to the voltage across the coil produced by the current flow. Subsequently, at output 3 the integrator 2 delivers signal D. This signal is sampled with a high clock frequency, e.g., 25 KHz, and the sample is fed into analog memory 4. Specifically, the initiating pulse A for this purpose initializes the voltage dependent timer 16 which at time $t_1$ from its output delivers a control signal to the clock 13. This control signal switches the clock 13 to the high scanning frequency of 25 KHz. After the expiration of the initiating delay of fifteen to twenty milliseconds, in addition to the maximum duration of the current through the patient of about ten milliseconds, that is after twenty-five to thirty milliseconds, the timer 16 terminates the control signal to the control input of clock 13 at time $t_3$ to switch clock 13 to the lower clock frequency of 250 Hz. The output signal of voltage dependent timer 16 is labelled E. If the initiating delay of the defilbrillator relay is independent from the amount of its supply voltage, timer 16 may operate it with a predetermined delay which does not depend on the voltage.

During the duration of the output pulse E of timer 16, the signal at the output 3 of integrator 2 is sampled with a high frequency and is stored in memory 4. The delay of twenty-five to thirty milliseconds ensures that in each case the total duration of the patient current is included and is written into the memory. At the end of this signal storing procedure, the stored signal is to be utilized in a time extended fashion and, in particular, is to be inserted into the ECG record. This ECG recording before defibrillation is performed with a recording strip speed of 2.5 cm/s for the signal delivered by the ECG electrodes, amplified and applied via terminal 10 and switch 11 to the writing or display input of the indicating device (not shown).

For the recording of the waveshape of the defibrillator current pulse, the recording of the ECG is interrupted at time $t_3$. For this purpose, a delay circuit 15 is connected to the output of the timer 16 via line 17. The operation of this delay circuit 15 is initiated when the delay period of timer 16 expires, i.e., at time $t_3$. Delay circuit 15 has a suitable delay time, e.g., one second, and its output on line 18 is shown in FIG. 2 as pulse F. During this pulse F, the control circuit 12 is actuated to interrupt the signal from ECG amplifier by opening switch 11 and closing switch 8 between amplifier 7 and the write input 9 of the ECG recorder. Thereafter, the output signal of the memory 4 is applied via amplifier 7 to the ECG recorder or indicator. When pulse E at the output of timer 16 terminates, as mentioned above, the clock frequency output of clock 13 is simultaneously switched to the lower frequency of 250 Hz. Consequently, the content of the memory 4 is read from the memory 4 and is displayed with a lower frequency, e.g., a frequency which is lower than the memory writing or storing frequency by a factor of 100. Accordingly, a time extended record G is derived from the voltage curve D originally taken from output 3 of integrator 2. This extended curve G clearly shows the waveshape of the defibrillator current pulse so that the amplitude and shape of the pulse can be evaluated. After the delay period of one second of the delay circuit 15, control circuit 12 is actuated to switch both switching paths 8 and 11 into their opposite positions so that the ECG signal from ECG input 10 is again applied to the input line 9 of the ECG recording device.

Curve H in the last line of FIG. 2 shows a typical curve of such a composite recording. Until time $t_3$, the electrocardiogram P, Q, R, S, T is recorded. The record H at time $t_3$ is interrupted by the switching of the switches 8, 11 by the control circuit 12 for one second corresponding to the duration of the output signal F of the delay circuit 15 whereby the electrocardiogram is replaced by the time extended record G of the defibrillator pulse. At time $t_5$, the switching of switches paths 8 and 11 back into their original position is achieved by the control circuit 12 so that the recording of the ECG is resumed.

In the illustrated embodiment, an analog memory 4 is used as intermediate memory for the defibrillator signal. It might be a charge coupled memory into which an input signal of ten milliseconds duration can be written. The memory 4 could also be a digital memory which in order to avoid any distortion of the pulse shape, a sufficient memory capacity of at least one hundred words of six bits each must be available. With a time extension factor of 100, the reading of the memory 4 lasts for about one second.

Accordingly, it may be seen that there has been provided, in accordance with the present invention, an improved defibrillator pulse indicator.

The embodiments of the invention in which an exclusive property or privilege is claimed are defined as follows:

1. An indicating device for a defibrillator, characterized by a coupling means for producing an electrical signal corresponding to a defibrillator current applied to a patient; a memory means for receiving and storing the electrical signal; a memory operation control circuit means for writing the signal into the memory means and for reading the signal from the memory means to produce a time extension of the signal and a control circuit means for selectively applying the time extension of the signal to an indicating means and which, for the duration of an indication of the time extended signal, interrupts the display of an ECG of the patient on the indicating means.

2. An indicating device according to claim 1 characterized in that the time extension factor is approximately 100.

3. An indicating device according to claim 1 characterized in that the memory means includes an analog memory.

4. An indicating device according to claim 1 characterized in that the memory is a digital memory for storing at least 100 words with six bit word lengths.

5. An indicating device according to claim 1 and characterized further in that the memory operation control circuit means includes a switchable clock means having a first and a second frequency clock signal output for providing a memory writing speed at the first frequency clock signal and a memory reading speed at the second frequency clock signal speed at the second frequency clock signal and a timer connected to said clock means and arranged to receive a defibrillation command signal and to produce in response thereto after a fixed time delay a clock frequency switch control signal for switching said clock means between said first and second frequency clock signal outputs, said time delay depending on the interval during which the control circuit means interrupts the display of an ECG on the indicating means.

6. An indicating device according to claim 5 and further characterized in that the control circuit means includes a delay circuit means for determining the duration of the ECG display interruption which is connected to receive the clock frequency switch control signal from the timer and to produce an output signal which controls the switching of the signal supplied to the indicating means to apply the time extended signal output of the memory means during the interruption of the display of an ECG of the patient on the indicating means.

7. An indicating device according to claim 5 and further characterized in that the control circuit means includes a first electrical signal switch for selectively connecting the time extended signal to the indicating means and a second electrical signal switch for selectively connecting the patient ECG to the indicating means and the output signal of the delay circuit means alternately operates the first and second electrical signal switches.

8. An indicating device according to claim 5 characterized in that the first frequency clock signal has a frequency approximately one hundred times greater than the frequency of the second frequency clock signal.

9. An indicating device according to claim 1 and further characterized in that the coupling means comprises a coupling winding arranged to respond to the defibrillator current and an integrator connected to the winding.

* * * * *